United States Patent [19]
Nishidate et al.

[11] Patent Number: 5,925,570
[45] Date of Patent: Jul. 20, 1999

[54] METHOD OF MEASURING METALS IN SAMPLES OF LIVING BODY

[75] Inventors: Kazuyoshi Nishidate; Hiroshi Suzuki; Youko Suzuki; Youko Koga, all of Tokyo, Japan

[73] Assignee: Iatron Laboratories, Inc., Tokyo, Japan

[21] Appl. No.: 08/885,629

[22] Filed: Jun. 30, 1997

Related U.S. Application Data

[62] Continuation of application No. 08/558,353, Nov. 16, 1995, abandoned, which is a continuation of application No. 08/094,019, filed as application No. PCT/JP92/01685, Dec. 24, 1992, abandoned.

[30] Foreign Application Priority Data

Dec. 25, 1991 [JP] Japan ..................................... 3-356423

[51] Int. Cl.$^6$ .................................................. G01N 21/78
[52] U.S. Cl. ................................ 436/74; 436/79; 436/84; 436/164; 436/177; 435/4; 435/962
[58] Field of Search .................................. 436/8, 17, 19, 436/73–84, 166, 174, 175, 177, 164; 435/4, 7.71, 962

[56] References Cited

U.S. PATENT DOCUMENTS

| | | | |
|---|---|---|---|
| 3,121,613 | 2/1964 | Bittner | 436/74 X |
| 3,754,865 | 8/1973 | Gindler | 436/74 |
| 3,934,977 | 1/1976 | Cleaver | 436/74 |
| 4,090,926 | 5/1978 | Matson | 436/742 X |
| 4,311,482 | 1/1982 | Workman, Jr. et al. | 436/18 |
| 4,618,587 | 10/1986 | Premoli et al. | 436/74 |
| 4,870,024 | 9/1989 | Musacchio et al. | 436/74 X |
| 4,968,630 | 11/1990 | Charlton et al. | 436/74 X |
| 5,219,760 | 6/1993 | Herrmann et al. | 436/74 X |
| 5,368,707 | 11/1994 | Henkens et al. | 436/77 |

FOREIGN PATENT DOCUMENTS

| | | |
|---|---|---|
| 48-3798 | 1/1973 | Japan . |
| 58-144750 | 8/1983 | Japan . |
| 59-23252 | 2/1984 | Japan . |
| 60-69552 | 4/1985 | Japan . |
| 61-124398 | 6/1986 | Japan . |
| 62-6170 | 1/1987 | Japan . |
| 64-0597 | 2/1989 | Japan . |
| 1301678 | 12/1989 | Japan . |
| 2142498 | 5/1990 | Japan . |

OTHER PUBLICATIONS

Chang, R. "Chemistry" First ed., Random House, N.Y. (1981) p. 670, 1981.
The Merck Index, Tenth Edition, Merck & Co., Inc., Rahway, N.J. (1983), p. 508, No. 3490, 1983.

*Primary Examiner*—Jeffrey Snay
*Attorney, Agent, or Firm*—Jordan and Hamburg LLP

[57] ABSTRACT

A method and a reagent for highly accurate measuring of trace amount of metals in a sample of living body. The method and the reagent for measuring metals in a sample of living body includes:

(1) a method for measuring metals in sample of living body, in which metals other than the objective metals of measurement are added to the measurement system to release the objective metals bonding to co-existing substances in the sample from the co-existing substances; and (2) a reagent for the measurement, in which metals other than the objective metals of the measurement are contained in a reagent for measuring metals in a sample of living body in order to release the objective metals bonding to the co-existing substances in the sample from the co-existing substances.

12 Claims, 4 Drawing Sheets

METHOD OF MEASURING METALS IN SAMPLES OF LIVING BODY

This application is a continuation of application Ser. No. 08/558,353 filed Nov. 16, 1995, now abandoned, which is a continuation of Ser. No. 08/094,019 filed Nov. 22, 1993, which is has been abandoned, which is a 371 of PCT/JP92/01685, filed on Dec. 24, 1992.

BACKGROUND OF THE INVENTION

The present invention relates to a method for measuring metals in sample of living body and a reagent for the measurement. More closely, the present invention relates to a method for measuring metals in samples of living body, in which metals other than the objective metals of measurement are added to the measurement system to release the objective metals bonding to co-existing substances in the sample from the co-existing substances, so that even trace objective metals in the sample can be measured with high accuracy; and a reagent for the measurement, in which metals other than the objective metals of the measurement are contained in a reagent for measuring metals in a sample of living body in order to release the objective metals bonding to the co-existing substances in the said sample from the co-existing substances.

In the field of clinical examination, the measurement of various kinds of metals in samples (components) of living body has frequently been used as indexes of disease diagnosis. For example, the measurement of magnesium as a diagnostic means for ischemic heart disease, hyperthyroidism, etc.; the measurement of iron as a diagnostic means for various kinds of anemia, chronic hepatopathy, etc.; the measurement of copper as a diagnostic means for disease of hepatic duct, anemia, etc.; the measurement of calcium as a diagnostic means for nephropyelitis, nephrosis, etc.; and the measurement of zinc as a diagnosis means for disease of circulatory organs, hemolytic anemia, etc. have usually been used. Other metals in living body including aluminum, nickel, manganese, chromium and so on have been also measured as indexes of various kinds of diseases.

The typical methods of measurement of these metals are, for example, atomic absorption spectrometry, emission spectrochemical analysis, X-ray fluorescence analysis, voltammetry, chelatometry, and the like. However, these methods are inadequate, particularly for daily examinations in the clinical examination field, since they not only require special, expensive apparatuses but also pretreatments of samples in such methods are troublesome. Therefore, recently, other various kinds of methods for measuring metals in living body have been developed. Among these, the methods for measuring major metals are, for example, as follows:

(i) As the method for measuring magnesium, there have been known the colorimetry in which titan yellow and xylidyl blue are used as color-producing agents, the enzymatic method which utilizes the activation of the enzyme reaction which is one of the physiological actions of magnesium (Japanese Patent Application Laid-open Nos. 124398/1986 and 30597/1989), and the like.

(ii) As the method for measuring iron, there have been frequently used the colorimetry in which bathophenanthroline and tripyridil-triazine are used as color-producing agents after reduction of free trivalent iron ions into bivalent iron ions with a reducing agent such as ascorbic acid and the like, and various kinds of other color-producing agents have been developed (Japanese Patent Application Laid-open Nos. 144750/1983 and 301678/1989).

(iii) As the method for measuring copper, there has been known the colorimetries in which bathocuproinedisulfonic acid and the like are used as color-producing agents after addition of reducing agent, and in which co-existing metals are masked and the 2-pyridylazo-aminophenol derivatives are then used as the color-producing agents (Japanese Patent Application Laid-open No. 69552/1985), and so on.

(iv) As the method for measuring calcium, there has been frequently used the colorimetry in which o-cresolphtalein complexone is used as a color-producing agent under alkaline condition. In addition, there has also been known the enzymatic method which utilizes the action of the enzyme activity as an activating factor which is one of the physiological actions of calcium (Japanese Patent Application Laid-open No. 142498/1990).

(v) As the method for measuring zinc, there has been frequently used the colorimetry in which zinc is reacted with [2-(5-bromo-2-pyridyl)azo]-5-(diethylamino)phenol in the presence of surfactants to form a complex compound.

The tested samples of living body for measurement of metals are those of blood (whole blood, blood serum, blood plasma, blood cell), urine, feces, hair, saliva, breast milk, and so on. Generally speaking, in clinical examination, metals contained in blood or urine are mainly measured.

In the measurement of metals in sample of living body using the above-mentioned metal measuring methods, color-producing agents which specifically react (bond) with the objective metals (i.e., chelating agents) are generally used. In the above-mentioned enzymatic methods, the enzymes which are specifically acted on by the objective metals are chosen, and the existing amount of metals are determined quantitatively according to the variability of the enzyme activity values.

However, in the measurement using the enzymatic methods and the colorimetries which utilize the color-producing agents mentioned above, desirable data sometimes cannot be obtained depending on samples. That is, the phenomenon, where the formability of a complex compound between the objective metal of measurement and the color-producing agent or the physiological action of the objective metals against the enzyme is inhibited or interfered with by some factors, sometimes can be observed.

Various factors are considered as causes of such phenomena. Among them, one possibility can be assumed that they may be caused by insufficient expression of the objective detection reaction, in which the objective metals of measurement in sample bond to some kinds of co-existing substances or secondary added substances in living body fluid and, consequently, the objective metals are subjected to the measurement system as the bonding state is maintained.

There are two types to be considered as such samples, which contain the bonding substances derived from patients themselves, and which contain the bonding substances derived from the treatment methods carried out after sampling from the patients. For example, in the samples containing the bonding substances derived from patients themselves, the substances are those derived from patients who have been dosed pharmaceutical medicines containing components having a metal-bondability (e.g., eliminant of renal calculus, detoxifying agents, metal-eliminating agents, anti-coagulants, etc.). In the samples containing the bonding substances derived from the treatment methods, the substances are, for example, those derived from various kinds of treatment agents charged in a blood sampling tube. Embodiments of such treatment agents include various derivatives from ethylenediamine (e.g., ethylenediaminetetraaketates, etc.), deferoxamine mesilate, citric acid, tartaric acid, etc., which largely affect the detection of the objective metals particularly. These are just a part of embodiments of substances which can bond to the objective metals in living body fluid or sample, and many other substances can be included.

In the measurement of metals in such samples, the objective metals of measurement can not induce the desired reaction in the detection system, depending on the combination of the objective metals and the co-existing substances mentioned above. Accordingly, the quantitative relationship between the color-production amount or the enzyme activity and the existing amount of the objective metals may be lost. For example, it is well known that sodium ethylenediaminetetraacetate (hereinafter, referred to as EDTA) can react with almost all metallic ions, except monovalent metallic ions, to form stable, water-soluble chelate complexes. However, when EDTA or other substances having similar natures to EDTA are co-existing in samples, they may form chelate complexes with the objective metals of measurement before detecting a reaction being occurred out and, therefore, the accurate measurement of the objective metals would become impossible. Particularly, in cases where the substances bonding to the objective metals of measurement are derived from patients themselves, it is impossible to predict previously in the clinical examination scene whether the samples contain disadvantageous factors to measurement of the objective metals or not. Therefore, when the question about the measured values occurs, re-sampling and re-examination may be naturally carried out, which may lead to burdens not only to patients but also in the scene of clinical examination.

In view of the foregoing, the present inventors have carried out extensive studies to provide a method and a reagent for measuring metals in vital components, in which the objective metals can be measured in high accuracy even in the presence of various interfering substances which may greatly affect the measured values in the measurement of metals in samples of living body. As a result, the present invention has been completed.

SUMMARY OF INVENTION

The present invention comprises the following:
(1) a method for measuring metals in sample of living body, in which metals other than the objective metals of measurement are added to the measurement system to release the objective metals bonding to co-existing substances in the sample from the co-existing substances; and
(2) a reagent for the measurement, in which metals other than the objective metals of the measurement are contained in a reagent for measuring metals in a sample of living body in order to release the objective metals bonding to the co-existing substances in the said sample from the co-existing substances.

The reason why the present invention comprises as mentioned above is as follows:
(a) As mentioned above, when the substances able to bond to the objective metals of measurement (hereinafter, referred to as interfering chelating substance), which are derived from patients themselves or the treatment methods, exist in the samples before the detecting reaction of the objective metals being occurred, the objective metals may exist in a state where they have been already bonded to the interfering chelating substances in the sample.

(b) In such sample, a sufficient reaction does not occur by addition of the reacting reagents of detection (e.g., color-producing substances) to the sample. Therefore, the colorimetry of the resulting color developments leads to inaccurate determined values, or the measurement itself sometimes become impossible. That is, such inaccuracy of measured values in the colorimetry, in which the color developments occurred by addition of the color-producing substances to the measurement system are detected, are caused by the information or hardness of formation of chelate complexes of the color-producing agents which develop color by specifically bonding to the objective metals.

In such case, by addition of substances which do not affect the reaction system, i.e., metals other than the objective metals of measurement which do not act or, if any, hardly act against the color-developing substances specific to the objective metals to the detecting reaction system, the bonds between the interfering chelating substances existing in sample and the objective metals become changed to the bonds between the interfering chelating substances and the metals other than the objective metals, and consequently, the objective metals are no longer influenced by the interfering chelating substances, to give an accurate measurement of the objective metals in living body fluid.

(c) In the methods applying the enzyme activities, the inaccuracy of the measured values are caused by the physiological action between the essential metals for expression of enzyme activity or the metals interfering with the enzyme activity and the enzyme is inhibited by the existence of the interfering chelating substances. In such case, the addition of metals other than the objective metals which do not inhibit or, if any, hardly inhibit the expression of enzyme activity in the detecting reaction system, makes it possible to measure the metals accurately in living body fluid.

Examples of the objective metals of measurement include potassium, calcium, magnesium, zinc, manganese, aluminum, cadmium, chromium, mercury, iron, copper, lead, nickel, selenium, bismuth, arsenic, etc. in vivo.

As mentioned above, recently, various kinds of metal indicator reagents specific to individual such metals have been developed, and the spectrooptical measurement can be carried out easily. A part of embodiments of the metal indicator reagents are shown in the following:

(a) magnesium: xylidyl blue, δ-hydroxy-5-quinolinesulfonic acid;
(b) calcium: o-cresolphtalein complexone;
(c) copper: bathocuproine, 2-[(5-bromo-2-pyridyl)azo]-5-[N-propyl-N-(3-sulfopropyl)amino]phenol, 2-(2-thiazolylazo)-5-N-ethyl-N-sulfopropylamino benzoic acid (TSAB);
(d) zinc: [2-(5-bromo-2-pyridyl)azo]-5-(diethylamino) phenol (5-Br-PADAP);
(e) iron: bathophenanthroline, tripyridil-triazine, ferrozine, o-phenanthroline, 2-nitroso-5-(N-propyl-N-sulfopropylamino)-phenol (Nitroso-PSAP);
(f) aluminum: 1-(1-hydroxy-4-methyl-2-phenylazo)-2-naphtol-4-sulfonic acid;
(g) cadmium: α, β, γ, δ-tetraphenylporphine tetrasulfonate;
(h) chromium: 3,3'-di(N-methyl-N-carboxymethylaminomethyl)-o-cresolsulfonphtalein;

(i) mercury: diphenylthiocarbazone;
(j) lead: diphenylthiocarbazone, 2,7-bis(4-methyl-2-sulfophenylazo)-1,8-dihydroxynaphthalene-3,6-disulfonic acid;
(k) nickel: 2-furildioxime; and
(l) selenium: 3,3-diaminobendizine.

Examples of enzymes used in the measurement of magnesium and calcium, in which the enzymatic reactions are applied, include glucokinase, hexokinase, amylase, glycerolkinase, isocitrate dehydrogenase, etc. These enzymes are derived from bacteria or yeast, but the origins of the enzymes are not limited in particular.

According to the present invention, in the measurement of metals in living body, metals other than the objective metals of the measurement, which have no reactivity or, if any, extremely little reactivity with the said color-producing metal indicator reagents, are arbitrarily selected and added to the measurement system.

For example, in case where iron in blood serum is measured using 2-(5-nitro-2-pyridylazo)-5-(N-propyl-N-sulfopropylamino)-phenol (NPS) as a color-producing metal indicator reagent, metals other than iron, which never bond to NPS to develop color, are added to the measurement system. A part of embodiments of such metals are, for example, lanthanum, manganese, terbium, yttrium, ytterbium, palladium, gallium, strontium, aluminum, etc.

On the other hand, in case where magnesium is measured by enzymatic method, metals other than magnesium, which never inhibit the physiological action of enzymes such as hexokinase, glucokinase, glycerolkinase, etc. and magnesium (i.e., expression of enzyme activity), are added to the measurement system. A part of embodiments of such metals are, for example, cobalt, aluminum, lanthanum, bismuth, nickel, etc., and many other metals may be used.

In addition, in case where zinc, copper, etc. are measured using color-producing metal indicator reagents, the present invention can be also applied according to the same idea as mentioned above.

The amount of metals other than the objective metals of measurement to be added to the reaction system, can be arbitrarily selected depending on the contents of interfering chelating substances and the objective metals of measurement. Metals other than the objective metals may be added in an amount at least enough to make the objective metals free from the interfering chelating substance, i.e., enough to make occur the objective reaction with the color-producing metal indicator reagent or enzyme. The amount of the metals other than the objective metals to be added should be adjusted according to amount and kinds of the objective metals of measurement, the composition of the reaction system and the interfering chelating substances, as required. Although it can not be said absolutely, the reagents containing metals other than the objective metals of measurement in an amount in the range from 5 $\mu$M to 2M, preferably 10 $\mu$M to 1M, may be prepared to be used in the measurement. The form of the metals other than the objective metals of measurement to be added is preferably the salts thereof, and they may be prepared within the above concentration range.

In the composition of the reaction system, the color-producing indicator reagents and enzymes may be contained within the known content range, and they are used preferably by dissolving in the known buffer solutions, i.e., the buffer solutions able to buffer the pH range in which the color developing reaction of metal indicator reagents and the expression of enzyme actions are possible (i.e., around the appropriate pH within pH 4 to 10), such as tris-hydrochloride buffer solution, acetate buffer solution, phosphate buffer solution, citrate buffer solution, Good's buffer solution, etc. The metals other than the objective metals of measurement may be co-existed in such solution or prepared as another reagents, if necessary, to be used for the measurement of metals in living body fluid. Such reagent thus prepared may contain known preservatives, stabilizers, various kinds of surfactants, reductants or oxidants.

On the other hand, the reagents for enzymatic methods can be preserved for a long time by freeze-drying using conventional known means, by consideration of stabilities of enzymes, etc. to be used. As mentioned above, according to the present invention, the objective metals of measurement can be easily measured without influence caused by the interfering chelating substances and, consequently, the metals in living body fluid can measured accurately.

DETAILED DESCRIPTION OF THE INVENTION

The present invention is further illustrated in detail by the following examples.

<EXAMPLE 1>

Measurement of Magnesium

To a commercially available control blood serum (NESCALL XA: a trade name produced by Nippon Shoji Co., Ltd.) of the known magnesium content (2.8 mg/dl), EDTA.2Na was added as a interfering chelating substance to obtain samples of concentration of 40, 80, 120, 160 and 200 mg/dl, respectively. Then, the following reagents were prepared to measure the magnesium content of the samples.

(Reagent 1)

100 mM Tris buffer solution which (pH 8.5) containing:

| ATP (adenosine triphosphate) | 10 mM |
| NADP (nicotinamide adenine dinucleotide phosphate) | 0.5 mM |
| Glucokinase | 0.35 U/ml |
| G6PDH (glucose-6-phosphate dehydrogenase) | 0.6 U/ml |
| GEDTA (glycoletherdiaminetetraacetic acid) | 0.4 mM. |

(Reagent 2)

100 mM Tris buffer solution which containing 10 mM of glucose (pH 8.5).

(Procedure)

To 5 μl of each control blood serum containing EDTA, 400 μl of Reagent 1 in which each of aluminum and cobalt as a metal other than the objective metal of measurement was contained in a concentration of 300 μM, respectively, was added, followed by heating to 37° C. To the resulting reaction solution, 100 μl of Reagent 2 was added, and the reaction was then started at 37° C. The absorbance of each sample was measured at 340 nm of wave length 2 to 3 minutes after the reaction being started. At the same time, another procedure was carried out in the same manner as the above procedure except using purified water instead of the control blood serum, and the resulting value was defined as a blank value. The magnesium content in each control blood serum with EDTA was calculated from the resulting absorbance value against that of the control blood serum without EDTA as a standard. Results are shown in FIGS. 1(a) and (b).

<COMPARATIVE EXAMPLE 1>

The magnesium content in each control blood serum was calculated in the same manner as Example 1 by using Reagent 1 of Example 1 as it was (i.e., without additional metals). Results are shown in FIG. 2.

Figure 1A:
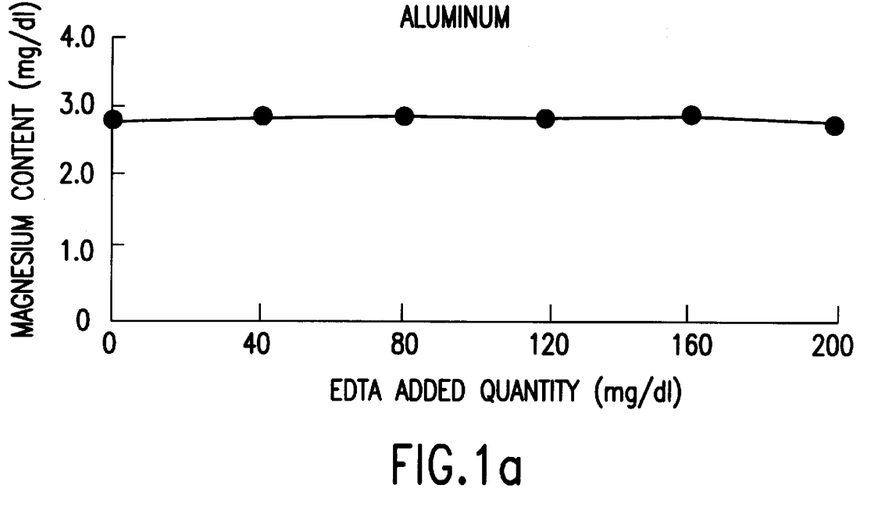
FIG. 1(a) illustrates a graph which represents the magnesium content in blood serum determined with addition of aluminum as a metal other than the objective metal of the measurement.
Figure 1B:
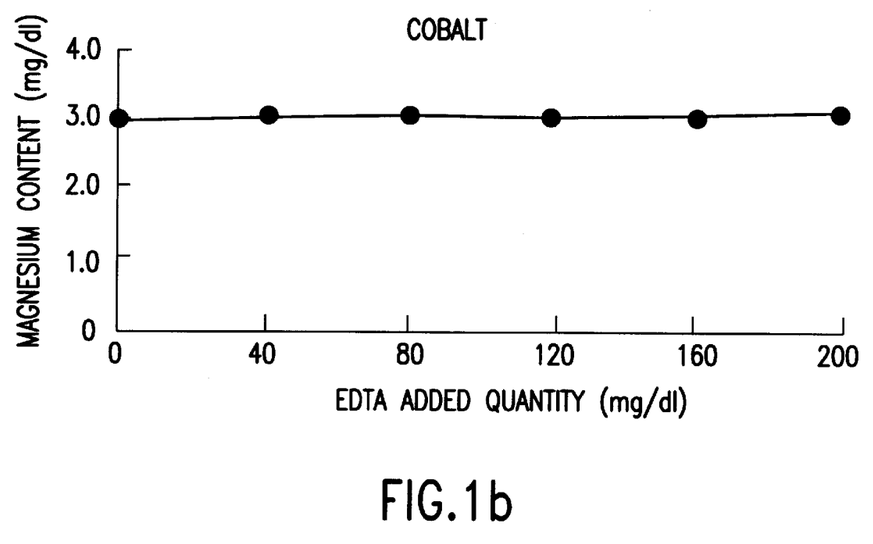
FIG. 1(b) illustrates a graph which represents the magnesium content in blood serum determined with addition of cobalt as a metal other than the objective metal of the measurement.
Figure 2:
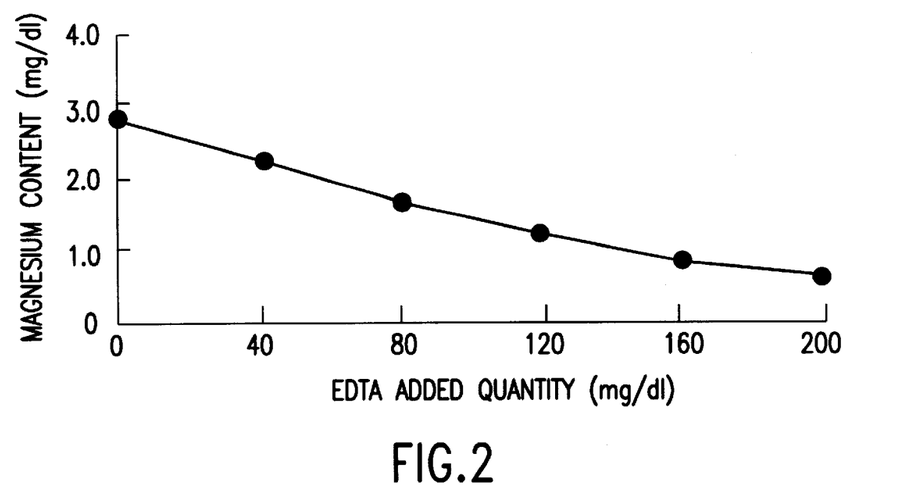
FIG. 2 illustrates a graph which represents the magnesium content in blood serum determined without addition of a metal other than the objective metal of the measurement. (Comparative example to FIG. 1.)

Apparently from the comparison between FIGS. 1(a) and (b) and FIG. 2, when metals other than magnesium (i.e., the objective metal of measurement) were added, the magnesium content can be measured accurately without influence of EDTA as an interfering chelating substance.

<EXAMPLE 2>

The commercially available control blood serum of Example 1 was diluted two-fold with purified water (i.e., 1.4 mg/dl of magnesium content), and EDTA.2Na was then added thereto to give samples containing 10, 20, 30, 40 and 50 mg/dl in a concentration of EDTA.2Na, respectively. The magnesium content of each resulting sample was measured according to the same procedure as Example 1 using Reagents 1 and 2 of Example 1.

Figure 3:
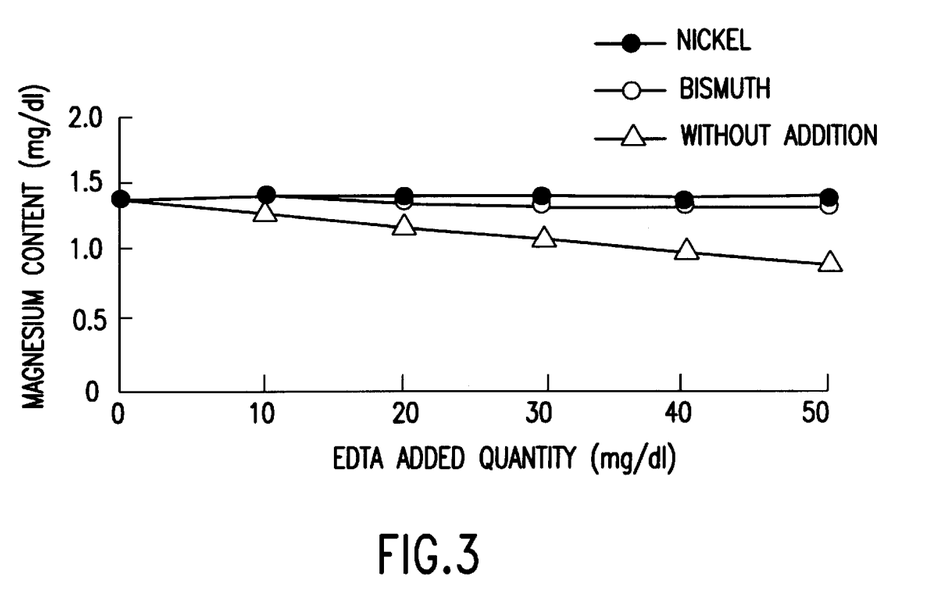
FIG. 3 illustrates a graph which represents the magnesium content in blood serum determined with addition of nickel and bismuth as metals other than the objective metal of the measurement.

In this procedure, Reagent 1 to be used was one which was prepared by adding nickel and bismuth as additional metals in a concentration of 150 μM, respectively. Results are shown in FIG. 3. Apparently from FIG. 3, the effect of addition of metals other than magnesium is confirmed.

<EXAMPLE 3>

Measurement of Iron

To the commercially available control blood serum (Q-PAK: a trade name produced by Hiland Co., Ltd.) of known iron content (150 μg/dl), EDTA.2Na was added as a interfering chelating substance, to give samples containing 40, 80, 120, 160 and 200 mg/dl in concentration of EDTA.2Na, respectively. The resulting samples were measured iron content using the reagents prepared as follows:

(Reagent 3)

0.5M Acetate buffer solution containing 0.2M of ascorbic acid (pH 4.0).

(Reagent 4)

An aqueous solution in which 200 mg of NPS being dissolved in purified water to a total volume of 1000 ml.

(Procedure)

Figure 4A:
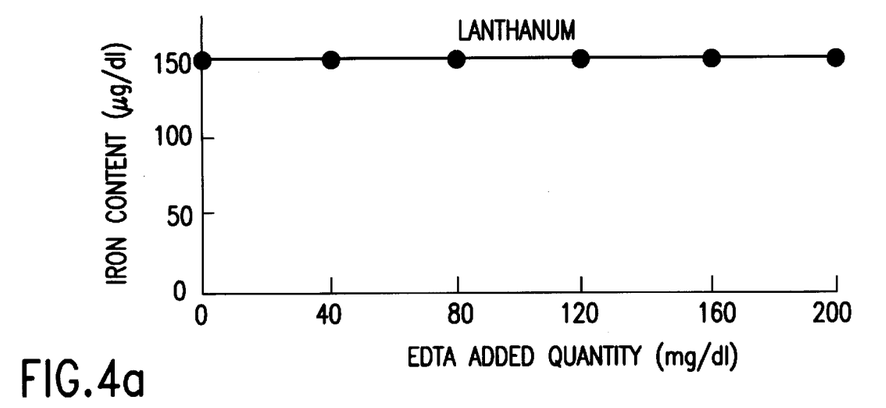
FIG. 4(a) illustrates a graph which represents the iron content in blood serum determined with addition of lanthanum as a metal other than the objective metal of the measurement.
Figure 4B:
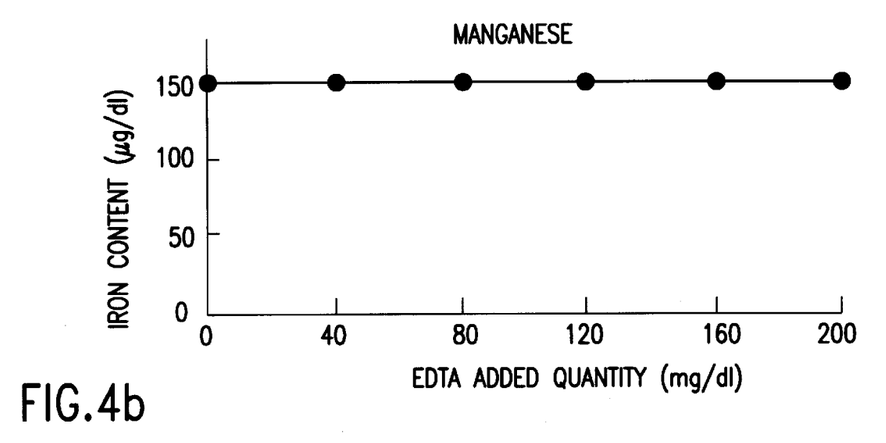
FIG. 4(b) illustrates a graph which represents the iron content in blood serum determined with addition of manganese as a metal other than the objective metal of the measurement.

To 100 μl of each control blood serum containing EDTA, 350 μl of Reagent 3 containing each one of lanthanum, manganese, terbium, yttrium, ytterbium, palladium, gallium, indium, strontium and aluminum in concentrations of 20 mM, respectively, was added, followed by heating to 37° C. 200 μl Of Reagent 4 was added thereto, and the reaction was then started at 37° C. The absorbance of each sample was measured at 590 nm of wave length 5 minutes after reaction being started. At the same time, another procedure was carried out in the same manner as the above procedure except using purified water instead of the control blood serum, and the resulting value was defined as a blank value. The iron content in each control blood serum with EDTA was calculated from the resulting absorbance value using the control blood serum without EDTA as a standard. Results obtained by using lanthanum and manganese as additional metals are shown in FIGS. 4(a) and (b). On the other hand, results obtained by using metals other than lanthanum and manganese as additional metals are shown in Table 1 below as measured values of iron content in the control blood serum containing 200 mg/dl of EDTA.

TABLE 1

| Metal | Iron Content (μg/dl) |
|---|---|
| Tb | 142.5 |
| Y | 146.7 |
| Yb | 143.3 |
| Pd | 148.1 |
| Ga | 150.8 |
| In | 147.7 |
| Sr | 142.0 |
| Al | 146.9 |

<COMPARATIVE EXAMPLE 2>

The iron content in each control blood serum was calculated in the same manner as Example 3 using Reagent 3 of the said Example 3 as it was (i.e., without additional metals). Results are shown in FIG. 5.

Figure 5:
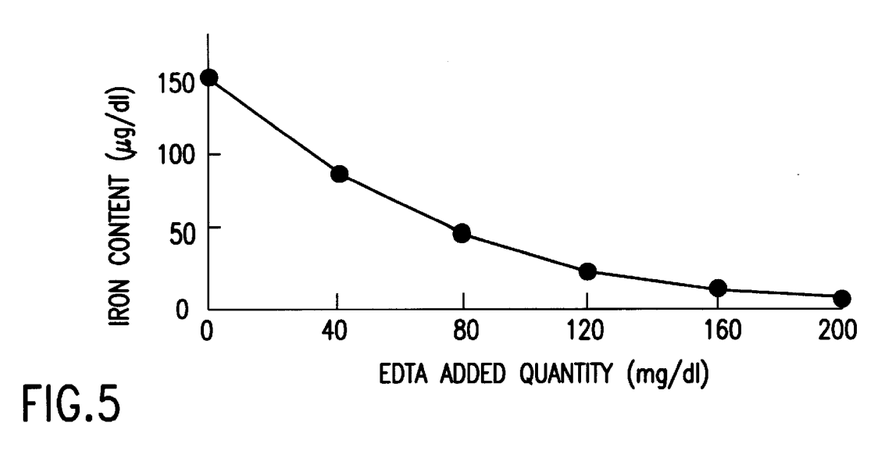
FIG. 5 illustrates a graph which represents the iron content in blood serum determined without addition of metal other than the objective metal of the measurement. (Comparative example to FIG. 4.)

Apparently from the comparison between FIGS. 4(a), (b) and Table 1 and FIG. 5, when metals other than iron (i.e., the objective metal of measurement) were added, the iron content can be measured accurately without influence of EDTA as a interfering chelating substance.

<EXAMPLE 4>

Measurement of Iron

A procedure was carried out in the same manner as Example 3 except using an aqueous solution in which 200 mg of Nitroso-PSAP was dissolved in purified water to a total volume of 1000 ml instead of Reagent 4 of said Example 3. In this procedure, the absorbance of each sample was measured at 760 nm of wave length. Results are shown in Table 2 below.

TABLE 2

| Metal | Iron Content (μg/dl) |
|---|---|
| La | 149.1 |
| Mg | 148.9 |
| Tb | 143.3 |
| Y | 145.2 |
| Yb | 144.1 |
| Pd | 146.3 |
| Ga | 147.6 |
| In | 148.9 |
| Sr | 144.4 |
| Al | 145.7 |

<EXAMPLE 5>

Measurement of Iron in Human Blood Serum

As to the human blood serum samples showing minus values of iron content in the measurement according to the conventional means, the following measuring test was carried out.

That is, although the data is not shown, Mg and Ca contents in the samples could be measured according to the conventional methods. Therefore, it was not considered that the EDTA-like substances (i.e., the substances showing a metal chelate effect) were present in the samples. However, according to the method of Example 3, the determination of the iron content in the samples was possible.

Results are shown in Table 3 below.

TABLE 3

| Sample | Conventional Method (μg/dl) | Present Method (μg/dl) |
|---|---|---|
| 1 | −7 | 96 |
| 2 | −35 | 22 |
| 3 | −43 | 110 |
| 4 | −16 | 49 |
| 5 | −48 | 93 |

In Table 3, Samples 1 to 4 are those prepared by adding manganese to Reagent 3 in a concentration of 20 mM, and Sample 5 is one prepared by adding lanthanum, instead of manganese, to Reagent 3 in a concentration of 20 mM.

<EXAMPLE 6>

Measurement of Copper 7.9 mg Of copper sulfate 5-hydrate salt was dissolved to purified water to a total volume of 1000 ml, to give a standard solution of 200 μg/dl of copper concentration. The resulting solution was further diluted with purified water to give a dilution line of 25, 50, 100, 150 and 200 μg/dl of copper concentrations. To each member of the dilution line, EDTA.2Na salt was added as a interfering chelating substance in a concentration of 200 mg/dl. The copper content was then measured using the following reagents:

(Reagent 5)

0.5M Acetate buffer solution (pH 4.0).

(Reagent 6)

An aqueous solution in which 200 mg of TSAB being dissolved in purified water to a total volume of 100 ml.

(Reagent 7)

0.5M Acetate buffer solution containing 30 mM of lanthanum (pH 4.0).

(Procedure)

To 100 μl of each member of the dilution lines containing EDTA, 2.0 ml of Reagent 5 was added, and then heated to 37° C. Then, 500 μl of Reagent 6 was further added to the resultant. After the reaction of the resulting solution being carried out at 37° C. for 5 minutes, the absorbance of each sample at 640 nm of wave length was measured.

Another test was carried out according to the same manner as the above procedure except using Reagent 7 instead of Reagent 5. Further another procedure was also carried out in the same manner as the above procedure except using purified water instead of the dilution line, and the resulting value was defined as a blank value. Results are shown in FIG. 6.

Figure 6:
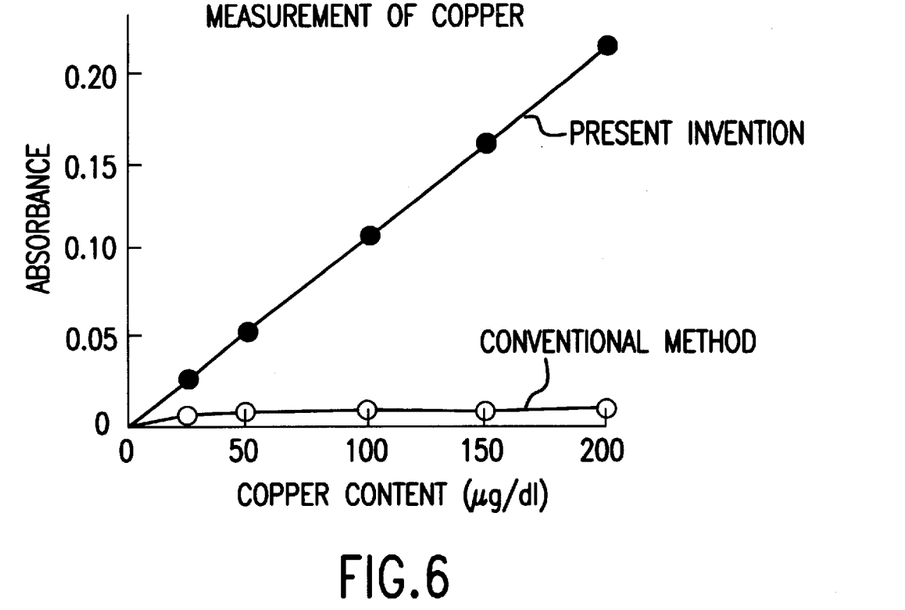
FIG. 6 illustrates a graph which represents the copper content determined with addition of lanthanum as a metal other than the objective metal of the measurement.

According to the FIG. 6, the method of the present invention apparently can measure the copper content more accurately compared to the conventional methods.

<EXAMPLE 7>

Measurement of Zinc 2.0 mg Of zinc powder was weighed accurately, and then 25 μl of hydrochloric acid was added thereto, followed by dissolving in purified water to a total volume of 1000 ml, to give a standard solution of 200 μg/dl of zinc concentration. The resulting solution was further diluted with purified water to give a dilution line of 25, 50, 150 and 200 μg/dl of zinc concentrations. To each member of the dilution line, EDTA.2Na salt was added as a interfering chelating substance in a concentration of 200 mg/dl. The zinc content of each sample was measured using the following reagents:

(Reagent 8)

0.5M Acetate buffer solution (pH 6.5).

(Reagent 9)

An aqueous solution in which 200 mg of 5-Br-PADAP being dissolved in purified water to a total volume of 500 ml.

(Reagent 10)

0.5M Acetate buffer solution containing 65 mM of lanthanum (pH 6.5).

(Procedure)

To 25 μl of each member of the dilution line containing EDTA, 2.0 ml of Reagent 8 was added, followed by heating to 37° C. Then, 200 μl of reagent 9 was further added to the resultant. After reaction of the resultant being carried out at 37° C for 5 minutes, the absorbance of each sample at 555 nm of wave length was measured. Another test was carried out in the same manner as the above procedure except using Reagent 10 instead of Reagent 8. Further another test was also carried out in the same manner as the above procedure except using purified water instead of the dilution line, and the resulting value was defined as a blank value. Results are shown in FIG. 7.

Figure 7:
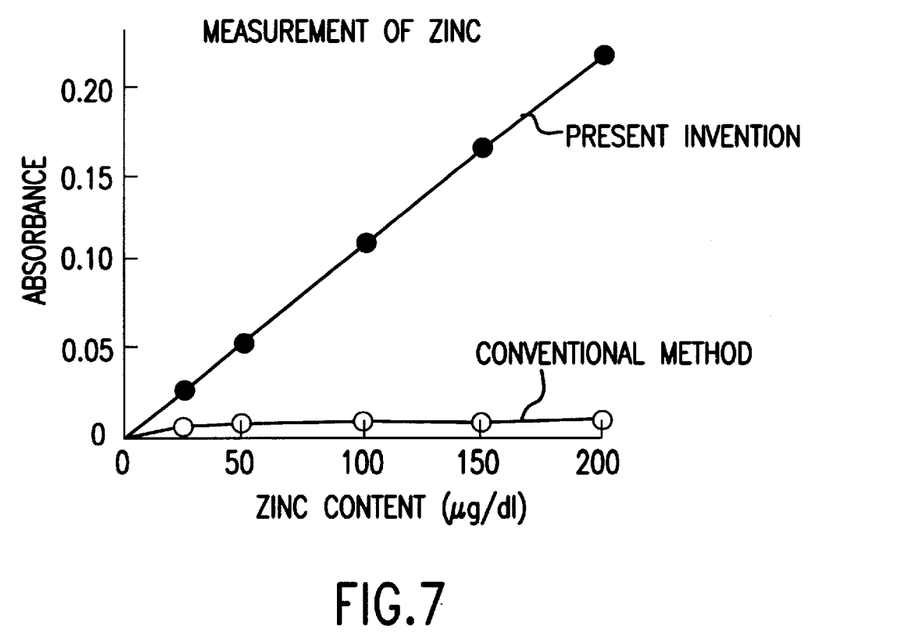
FIG. 7 illustrates a graph which represents the zinc content determined with addition of lanthanum as a metal other than the objective metal of the measurement.

According to FIG. 7, it is evident that the method of the present invention can measure the zinc content more accurately compared to the conventional methods.

Industrial Applicability

According to the present invention, the method and the reagents for measuring metals in samples of living body, which comprises as mentioned above, can release the objective metals of measurement bonding to the co-existing substances in the samples from the co-existing substances easily. Therefore, even a trace amount of metals in samples of living body can be measured in high accuracy, and the method and the reagents of the present invention can be widely utilized in the field of clinical examination taking charge of diagnosis of human disease.

We claim:

1. A method for calorimetrically measuring metals in a sample of living tissue or fluid, comprising:

adding metals, other than objective metals of measurement, to the measurement system, said objective metals of measurement being selected from the group consisting of magnesium, iron, zinc, potassium, calcium, manganese, aluminum, cadmium, chromium, mercury, copper, lead, nickel, selenium, bismuth and arsenic and said metals other than the objective metals of measurement being different from the objective metals and being at least one selected from the group consisting of lanthanum, manganese, terbium, yttrium, ytterbium, palladium, gallium, indium, strontium, aluminum, cobalt and bismuth;

releasing the objective metals bonding to interfering substances, which are in the sample, from the interfering substances, the metals other than the objective metals bonding to the interfering substances;

adding a color-producing substance for specifically binding to the objective metals; and spectroscopically detecting a signal derived from the color-producing substance.

2. The method of claim 1, wherein the metals other than the objective metals of measurement are added in an amount ranging from about 5 $\mu$M to about 2M.

3. A method for measuring metals in a sample of living tissue or fluid quantitatively by determining the activity of an enzyme, comprising the steps of:

(A) adding metals other than objective metals of measurement to the sample for releasing the objective metals from interfering substances, the metals other than the objective metals bonding to the interfering substances, the objective metals of measurement being selected from the group consisting of magnesium, potassium, calcium, sodium and phosphorous and the metals other than the objective metals of measurement being different from the objective metals and being at least one selected from the group consisting of lanthanum, manganese, terbium, yttrium, ytterbium, palladium, gallium, indium, strontium, aluminum, cobalt and bismuth;

(B) adding an enzyme to the sample; and (C) spectroscopically detecting a signal derived from the activity of the enzyme.

4. The method of claim 3, wherein the metals other than the objective metals of measurement are added in an amount ranging from about 5 $\mu$M to about 2M.

5. A method for calorimetrically measuring metals in a sample of living tissue or fluid, comprising:

adding metals, other than objective metals of measurement, to the measurement system, said metals other than the objective metals of measurement being different from the objective metals and being at least one selected from the group consisting of lanthanum, manganese, terbium, yttrium, ytterbium, palladium, gallium, indium, strontium, aluminum, cobalt and bismuth;

releasing the objective metals bonding to interfering substances, which are in the sample, from the interfering substances, the metals other than the objective metals bonding to the interfering substances;

adding a color-producing substance for specifically binding to the objective metals; and spectroscopically detecting a signal derived from the color-producing substance.

6. The method of claim 5 wherein the metals other than the objective metals of measurement are added in an amount ranging from about 5 $\mu$M to about 2M.

7. The method of claim 5, wherein said objective metals of measurement are selected from the group consisting of magnesium, iron, zinc, potassium, manganese, aluminum, chromium, mercury, nickel, selenium, bismuth and arsenic.

8. A method for measuring metals in a sample of living tissue or fluid quantitatively by determining the activity of an enzyme, comprising the steps of:

(A) adding metals other than objective metals of measurement to the sample for releasing the objective metals from interfering substances, the metals other than the objective metals bonding to the interfering substances, the metals other than the objective metals of measurement being different from the objective metals and being at least one selected from the group consisting of lanthanum, manganese, terbium, yttrium, ytterbium, palladium, gallium, indium, strontium, aluminum, cobalt and bismuth;

(B) adding an enzyme to the sample; and (C) spectroscopically detecting a signal derived from the activity of the enzyme.

9. The method of claim 7, wherein the objective metals of measurement are selected from the group consisting of magnesium, potassium, calcium, sodium and phosphorous.

10. The method of claim 8, wherein the metals other than the objective metals of measurement are added in an amount ranging from about 5 $\mu$M to about 2M.

11. A method for measuring metals in a sample of living tissue or fluid, comprising adding metals other than objective metals of measurement to the sample for releasing the objective metals from interfering substances, the metals other than the objective metals bonding to the interfering substances, the metals other than the objective metals of measurement being different from the objective metals and being at least one selected from the group consisting of lanthanum, manganese, terbium, yttrium, ytterbium, palladium, gallium, indium, strontium, aluminum, cobalt and bismuth; and measuring the objective metals of measurement.

12. The method of claim 11, wherein the metals other than the objective metals of measurement are added in an amount ranging from about 5 $\mu$M to about 2M.

* * * * *